United States Patent
Mougin

(10) Patent No.: US 6,737,071 B2
(45) Date of Patent: May 18, 2004

(54) COMPOSITION COMPRISING POLYMERS HAVING A STAR STRUCTURE, THE POLYMERS, AND THEIR USE

(75) Inventor: Nathalie Mougin, Paris (FR)

(73) Assignee: L'Oreal, S.A. (FR)

(*) Notice: Subject to any disclaimer, the term of this patent is extended or adjusted under 35 U.S.C. 154(b) by 0 days.

(21) Appl. No.: 10/139,530

(22) Filed: May 7, 2002

(65) Prior Publication Data

US 2002/0168332 A1 Nov. 14, 2002

Related U.S. Application Data

(62) Division of application No. 09/544,397, filed on Apr. 5, 2000.

(30) Foreign Application Priority Data

Apr. 6, 1999 (FR) .............................. 99 04254

(51) Int. Cl.⁷ ................. C08L 35/00; C08F 297/00; C08F 2/00; C08G 85/00
(52) U.S. Cl. .................. 424/401; 525/94; 525/299; 526/72; 526/73; 526/303.1
(58) Field of Search ............... 424/401; 525/94, 525/299; 526/72, 73, 303.1

(56) References Cited

U.S. PATENT DOCUMENTS

| | | |
|---|---|---|
| 3,907,984 A | 9/1975 | Calvert et al. |
| 4,659,783 A | 4/1987 | Spinelli ................ 525/293 |
| 5,221,534 A | 6/1993 | DesLauriers et al. .... 424/78.03 |
| 5,310,807 A * | 5/1994 | Antonelli et al. ........... 525/286 |
| 5,362,813 A | 11/1994 | Antonelli et al. ........... 525/286 |
| 5,371,147 A | 12/1994 | Spinnelli et al. ............ 525/288 |
| 5,525,636 A | 6/1996 | Henn et al. .................. 521/59 |
| 5,527,524 A | 6/1996 | Tomalia et al. ............. 424/1.33 |
| 5,552,491 A | 9/1996 | Mishra et al. |
| 5,804,664 A * | 9/1998 | Kennedy et al. ............ 525/314 |
| 5,807,937 A | 9/1998 | Matyjaszewski et al. |
| 5,849,278 A | 12/1998 | Piot et al. .................... 424/70.7 |
| 5,900,464 A | 5/1999 | Letchford et al. |
| 5,919,442 A | 7/1999 | Yin et al. ................... 424/78.18 |
| 5,986,020 A | 11/1999 | Campbell et al. ............. 526/64 |
| 6,001,342 A | 12/1999 | Forestier et al. ........... 424/76.1 |
| 6,013,735 A | 1/2000 | Mishra et al. |
| 6,024,948 A | 2/2000 | Samain et al. ........... 424/70.16 |
| 6,090,902 A | 7/2000 | Kuo et al. .................... 526/279 |
| 6,113,882 A | 9/2000 | Mougin et al. ............... 424/47 |
| 6,124,411 A | 9/2000 | Matyjaszewski et al. ... 526/111 |
| 6,132,736 A | 10/2000 | Mellul et al. ................ 424/401 |
| 6,139,827 A * | 10/2000 | Cohen et al. ............ 424/70.16 |
| 6,150,468 A | 11/2000 | Schoenberg et al. ........ 525/222 |
| 6,221,991 B1 | 4/2001 | Letchford et al. |
| 6,476,124 B1 | 11/2002 | Mougin ........................ 525/64 |
| 6,552,146 B1 | 4/2003 | Mougin ....................... 526/319 |

FOREIGN PATENT DOCUMENTS

| | | |
|---|---|---|
| DE | 43 28 004 | 2/1995 |
| DE | 196 02 540 | 7/1997 |
| EP | 0 557 196 | 8/1993 |
| EP | 0 639 371 | 2/1995 |
| EP | 0 704 477 | 4/1996 |
| WO | WO 86/00626 | 1/1986 |
| WO | WO 96/17886 | 6/1996 |
| WO | WO 96/33690 | 10/1996 |
| WO | WO 96/36323 | 11/1996 |
| WO | WO 97/18247 | 5/1997 |

OTHER PUBLICATIONS

Co–pending Application No. 09/544,394; Title: Composition Comprising Polymers Having a Star Structure, The Polymers, and Their Use, Inventors: Nathalie Mougin, U.S. Filing Date: Apr. 5, 2000.
Co–pending Application No. 10/345,977; Title: Composition Comprising Polymers Having a Star Structure, The Polymers, and Their Use, Inventors: Nathalie Mougin, U.S. Filing Date: Jan. 17, 2003.
Co–pending Application No. 10/656,238; Title: Composition Comprising Polymers Having a Star Structure, The Polymers, and Their Use, Inventors: Nathalie Mougin, U.S. Filing Date: Sep. 8, 2003.
Co–pending Application No. 10/247,362; Title: Composition Comprising Polymers Having a Star Structure, The Polymers, and Their Use, Inventors: Nathalie Mougin, U.S. Filing Date: Sep. 20, 2002.
English Language esp@cenet Abstract of EP 0 557 196.
English Language esp@cenet Abstract of WO 96/17886.
English Language esp@cenet Abstract of EP 0 704 477.
Product Information for Styrolux 684D (Sep. 1998) available from the BASF Company at www.basf.de (last checked Apr. 2002).
"Polymer Chemistry," second edition, 1988 Seymour et al., Marcel Dekker, Inc., pp. 354–358.
"Polymer Handbook," third edition, 1992 John Willey and Sons, Brandrup et al., p. II–193.
English language Derwent Abstract of DE 43 38 004.
English language Derwent Abstract of DE 196 02 540.

* cited by examiner

*Primary Examiner*—Sreeni Padmanabhan
*Assistant Examiner*—Lauren Q. Wells
(74) *Attorney, Agent, or Firm*—Finnegan, Henderson, Farabow, Garrett & Dunner L.L.P.

(57) ABSTRACT

A composition, in particular a cosmetic composition, comprising, in an appropriate medium, at least one polymer with a highly specific ordered structure is disclosed. These compositions find a specific application in the field of make-up and are capable of being applied to the skin, semi-mucous membranes and/or mucous membranes. In particular, these compositions can be provided in the form of a transfer-free make-up composition.

23 Claims, No Drawings

COMPOSITION COMPRISING POLYMERS HAVING A STAR STRUCTURE, THE POLYMERS, AND THEIR USE

This is a division of application Ser. No. 09/544,397, filed Apr. 5, 2000, which is incorporated herein by reference.

The present invention relates to a composition, in particular a cosmetic or pharmaceutical composition, comprising, in an appropriate medium, at least one polymer with a highly specific ordered structure. These compositions find a specific application in the field of make-up and are capable of being applied to the skin, semi-mucous membranes and/or mucous membranes.

Compositions to be applied to the skin, semi-mucous membranes and/or mucous membranes, such as lipsticks and foundations, are generally provided in the form of a stick, soft paste or cast paste and comprise fatty substances, such as oils, pasty compounds and/or waxes, and a particulate phase generally composed of fillers and pigments.

However, some of these compositions exhibit the disadvantage of transferring. This is understood to mean that the composition is capable of being deposited, at least partly, on certain substrates with which it is brought into contact, such as, for example, a glass, a cup, an item of clothing or the skin. On being deposited, the composition leaves a mark on the substrate. This therefore results in a mediocre persistence of the composition on the skin, semi-mucous membranes or mucous membranes and the need to regularly renew its application.

Furthermore, the appearance of unacceptable marks on some items of clothing and in particular on blouse collars can dissuade some women from using this type of make-up.

Another disadvantage of these compositions lies in the problem of migration. This is because it has been found that some compositions have a tendency to spread inside the fine lines and/or wrinkles of the skin, in the case of foundations; in the fine lines which surround the lips, in the case of lipsticks; and in the folds of the eyelid, in the case of eyeshadows. There has also been observed, in particular in the case of eyeshadows, the appearance of streaks in the make-up, generated by the movements of the eyelids. It has also been found that eyeliners can also run. All these phenomena produce an unsightly effect which it is very clearly desirable to avoid.

For some years, many cosmetic scientists have been interested in "transfer-free" cosmetic compositions, in particular lipstick or foundation compositions. Thus, "transfer-free" liquid lipstick compositions have been envisaged comprising from 1 to 70% by weight of silicone resin with silicate repeat units, from 10 to 98% by weight of a volatile silicone oil and pulverulent fillers. However, the film obtained on the lips after evaporation of the silicone oil exhibits the disadvantage of becoming uncomfortable over time (feeling of dryness and tightness).

"Transfer-free" lipsticks are also known comprising a volatile silicone and a liquid silicone resin comprising a pendant esterified chain having at least 12 carbon atoms. The lipstick film exhibits in particular the disadvantage of lacking comfort on application, in particular of being too dry.

Furthermore, cosmetic make-up compositions comprising film-forming polymers in aqueous solution have been described; however, these compositions are sensitive to water and therefore cannot, in particular, be applied to the lips. When the polymers are dissolved in alcoholic or aqueous/alcoholic media, it has been found that the composition obtained can lead to problems of irritation and/or dehydration of the skin, resulting in a degree of discomfort for the user.

A composition capable of being applied to the skin, semi-mucous membranes and/or mucous membranes is also known, for example from the document EP820,764, comprising, in a polymeric system, an aqueous dispersion of particles of film-forming polymer, the polymeric system making it possible to obtain a film having a Young's modulus of less than approximately 200 MPa.

The aim of the present invention is to provide a composition which does not exhibit the disadvantages of the prior art and which is in particular comfortable to apply and to wear while not being sticky to the touch (absence of tack).

This is because it has been found that compositions intended to be applied to the skin, such as foundations, lipsticks or care compositions, which comprise film-forming polymers generally cannot be simultaneously comfortable to wear and not very sticky to the touch, even after drying. The inventors have for the first time demonstrated that, by using the novel polymers which are the subject-matter of the present invention, it is possible to obtain a cosmetically satisfactory compromise between these two properties, while retaining, in the compositions, the appropriate cosmetic qualities expected by the consumer.

Thus, a subject-matter of the present invention is a polymer with a "star" structure represented by the following formula (I):

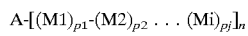

$$A\text{-}[(M1)_{p1}\text{-}(M2)_{p2} \ldots (Mi)_{pj}]_n$$

in which:

A represents a polyfunctional centre, with a functionality of "n", n being an integer greater than or equal to 2, $[(M1)_{p1}\text{-}(M2)_{p2} \ldots (Mi)_{pj}]$ represents a polymer chain, also known as a "branch", composed of identical or different polymerized monomers Mi having a polymerization index pj, each branch being identical or different and being grafted covalently to the centre A;

i being greater than or equal to 2 and pj being greater than or equal to 2; the polymer with a star structure comprising:

one or more monomers Mi chosen from polymerized monomers Mk, which may be identical or different, wherein a homopolymer formed by the corresponding polymerized monomers Mk has a Tg of greater than or equal to 0° C., preferably of greater than or equal to 5° C. and even better still of greater than or equal to 20° C.; this or these monomers Mk being present, in the final polymer, in a minimum amount of approximately 40% by weight, preferably in an amount of between 50 and 99% by weight and even better still in an amount of 60–90% by weight with respect to the total weight of monomers; and the polymer with a star structure furthermore comprising one or more monomers Mi chosen from polymerized monomers Mj, which may be identical or different, wherein a homopolymer formed by the corresponding polymerized monomers Mj has a Tg of less than or equal to 0° C., preferably of less than or equal to −10° C. and even better still of less than or equal to −15° C.; this or these monomers Mj being present, in the final polymer, in a maximum amount of approximately 60% by weight, preferably in an amount of between 1 and 50% by weight and even better still in an amount of 10–40% by weight with respect to the total weight of monomers.

Another subject-matter of the invention is a composition comprising, in a physiologically acceptable medium, at least one polymer as defined above.

Another subject-matter of the invention is a process for the cosmetic treatment of keratinous substances, such as the skin, hair, scalp, eyelashes, eyebrows, nails or lips, characterized in that it comprises applying, to the latter, a cosmetic composition as defined above.

Another subject-matter of the invention is the use of at least one polymer as above in a cosmetic composition or for the preparation of a pharmaceutical composition for decreasing, indeed even eliminating, the transfer of the composition film which has been deposited.

The compositions according to the invention exhibit a light texture and are very comfortable to wear throughout the day.

Furthermore, these compositions make it possible to obtain a film with very good hold, which does not transfer and which does not stain a substrate with which it would be in contact, and which does not migrate over time.

The film is soft, supple, elastic and flexible on the skin; it follows the movements of the substrate on which it is deposited, without cracking and/or detaching. In particular, it adheres perfectly to the lips of the face.

Another advantage contributed by the present invention is that it is possible to obtain a non-sticky and comfortable transfer-free film.

The composition according to the invention can be readily applied and spreads easily, in particular on the lips of the face. The composition according to the invention in particular finds an especially advantageous application in the field of making up human skin, mucous membranes and/or semi-mucous membranes.

The term "mucous membrane" is understood to mean in particular the internal part of the lower eyelid; the term "semi-mucous membranes" is understood to mean more particularly the lips of the face.

Thus, the composition according to the invention finds a preferred application in the field of products for making up the lips of the face, in particular as lipstick. It also finds another advantageous application in the field of foundations, face powders or eyeshadows.

The composition according to the invention therefore comprises a polymer, the "star" structure of which can be illustrated, in a general way, by the following formula (I):

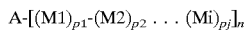

in which:
   A represents a polyfunctional centre, with a functionality of "n", n being an integer greater than or equal to 2, preferably of between 4 and 10,
   $[(M1)_{p1}\text{-}(M2)_{p2} \ldots (Mi)_{pj}]$ represents a polymeric chain, also known as a "branch", composed of identical or different polymerized monomers Mi having a polymerization index pj, each branch being identical or different and being grafted covalently to the centre A;
   i being greater than or equal to 2, preferably of between 2 and 10; and
   pj being greater than or equal to 2, preferably of between 10 and 20,000.

The polymer chains are preferably provided in the form of blocks with a molecular mass of greater than or equal to 500 which can range up to 2,000,000.

In a preferred embodiment, the polymer used in the context of the present invention can be obtained by controlled radical polymerization, also known as "living" radical polymerization. This technique makes it possible in particular to overcome the limitations inherent in conventional radical polymerization, that is to say that it makes it possible in particular to control the length of the chains of the polymer which is formed and therefore to obtain block structures.

The controlled radical polymerization makes it possible to reduce the reactions in which the growing radical species is deactivated, in particular the termination stage, which reactions, in conventional radical polymerization, interrupt the growth of the polymer chain in an irreversible and uncontrolled way.

In order to decrease the probability of termination reactions, provision has been made to block, in a temporary and reversible way, the growing radical species by forming so-called "dormant" active species with the aid of a bond of low dissociation energy.

In particular, mention may be made of the possibility of using bonds of C—ONR type (by reaction with a nitroxyl); this is illustrated in particular by the article "Synthesis of nitroxy-functionalized polybutadiene by anionic polymerization using a nitroxy-functionalized terminator", published in Macromolecules, 1997, volume 30, pp. 4238–4242.

Mention may also be made of the possibility of using bonds of C-halide type (in the presence of metal/ligand complex). This is then described as atom transfer radical polymerization, also known under the abbreviation ATRP. This type of polymerization is reflected in control of the mass of the polymers which are formed and in a low polydispersity index by weight of the chains.

Atom transfer radical polymerization is generally carried out by polymerization:
   of one or more radically polymerizable monomers, in the presence
   of an initiator having at least one radically transferable atom or group,
   of a compound comprising a transition metal capable of participating in a reduction stage with the initiator and a "dormant" polymer chain, and
   of a ligand, which can be chosen from compounds comprising a nitrogen (N), oxygen (O), phosphorus (P) or sulphur (S) atom, which compounds are capable of coordinating via a σ bond to the compound comprising a transition metal, or from compounds comprising a carbon atom, which compounds are capable of coordinating via a π or σ bond to the compound comprising a transition metal, the formation of direct bonds between the compound comprising a transition metal and the polymer in the course of formation being avoided.

This process is illustrated in particular in Application WO97/18247, the teaching of which can be drawn upon by a person skilled in the art in preparing the polymers coming within the scope of the present invention.

The nature and the amount of the monomers, initiator(s), compound(s) comprising the transition metal and ligand(s) will be chosen by a person skilled in the art on the basis of his overall knowledge, according to the result desired.

In particular, the monomers "M" (Mi, Mk, and Mj) can be chosen, alone or as a mixture, from radically polymerizable compounds comprising ethylenic unsaturation corresponding to the formula:

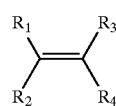

in which $R_1$, $R_2$, $R_3$ and $R_4$ are, independently of one another, chosen from:

a hydrogen atom;

a halogen atom;

a linear or branched alkyl radical having 1 to 20, preferably 1–6, more preferably 1–4, carbon atoms which is optionally substituted by one or more halogens and/or one or more —OH radicals;

a linear or branched alkenyl or alkynyl radical having 2 to 10, preferably 2–6, more preferably 2–4, carbon atoms which is optionally substituted by one or more halogens;

a cyclic hydrocarbonaceous (cycloalkyl) radical having 3 to 8 carbon atoms which is optionally substituted by one or more halogen, nitrogen, sulphur or oxygen atoms;

a radical chosen from CN, C(=Y)$R^5$, C(=Y)$NR^6R^7$, YC(=Y)$R^5$, cyclic NC(=Y)$R^5$, $SOR^5$, $SO_2R^5$, $OSO_2R^5$, $NR^8SO_2R^5$, $PR^5_2$, P(=Y)$R^5_2$, $YPR^5_2$, YP(=Y)$R^5_2$, $NR^8_2$, which can be quaternized with an additional $R^8$ group, aryl and heterocyclyl, with:

Y represents O, S or $NR^8$ (preferably O), $R^5$ represents a linear or branched alkyl, alkylthio or alkoxy radical having 1–20 carbon atoms; an OH radical; an OM' radical with M'=alkali metal; an aryloxy radical or a heterocyclyloxy radical;

$R^6$ and $R^7$ represent, independently of one another, H or a linear or branched alkyl radical having 1–20 carbon atoms; it being given that $R^6$ and $R^7$ can be joined to form an alkylene group having 2–7, preferably 2–5, carbon atoms;

$R^8$ represents H, a linear or branched alkyl radical having 1–20 carbon atoms or an aryl radical;

a —COOR radical, in which R is a linear or branched alkyl radical having 1 to 20, preferably 1–6, carbon atoms which is optionally substituted by one or more halogens;

a —CONHR' radical, in which R' is hydrogen or a saturated or unsaturated, linear or branched, hydrocarbonaceous radical having 1 to 20, preferably 1–6, carbon atoms which is optionally substituted by one or more halogens, nitrogens and/or oxygens;

an —OCOR" radical, in which R" is hydrogen or a saturated or unsaturated, linear or branched, hydrocarbonaceous radical having 1 to 20 carbon atoms which is optionally substituted by one or more halogens, nitrogens and/or oxygens;

a radical comprising at least one silicon atom and in particular radicals such as: an —R-siloxane radical, a —CONHR-siloxane radical, a —COOR-siloxane radical or an —OCO—R-siloxane radical, in which radicals R is a linear or branched alkyl, alkylthio, alkoxy, aryloxy or heterocycloxy radical having 1–20 carbon atoms.

The term "siloxane" is understood to mean a compound comprising (—Si$R^a R^b$O—)$_n$ units, in which units $R^a$ and $R^b$ can represent, independently of one another, a hydrogen; a halogen; a saturated or unsaturated, linear or branched, hydrocarbonaceous radical having 1 to 36 carbon atoms which is optionally substituted by one or more halogens, nitrogens and/or oxygens; or a cyclic hydrocarbonaceous radical having 1 to 20 carbon atoms; n being greater than or equal to 1.

For the purpose of this invention, the term "independent," when used to describe the relationship of radicals, atoms, substituents, functional groups, etc., means that each of the radicals, atoms, substituents, functional groups, etc. may be the same or different from the other, or some radicals, atoms, substituents, functional groups, etc., may be the same while the others may be different.

Mention may in particular be made of polydimethylsiloxanes (PDMSs) comprising 1 to 200, preferably less than 100, repeat units.

Furthermore, $R^1$ and $R^3$ can be connected to one another so as to form a ring of formula (CH$_2$)$_n$ which can be substituted by one or more halogens and/or oxygens and/or nitrogens and/or by alkyl radicals having 1 to 6 carbon atoms.

The term "aryl" or "heterocyclyl" is understood to mean the definition commonly understood by a person skilled in the art and which may be illustrated by the prior art WO97/18247.

Preferably, the monomers M can be chosen from:

acrylic or methacrylic esters obtained from linear, branched or cyclic aliphatic alcohols and/or from aromatic alcohols, preferably $C_1$–$C_{20}$ alcohols, such as methyl (meth)acrylate, ethyl (meth)acrylate, propyl (meth)acrylate, butyl (meth)acrylate, isobutyl (meth)acrylate or tert-butyl (meth)acrylate;

$C_1$–$C_4$ hydroxyalkyl (meth)acrylates, such as 2-hydroxyethyl (meth)acrylate or 2-hydroxypropyl (meth)acrylate;

ethylene glycol, diethylene glycol or polyethylene glycol (meth)acrylates with a hydroxyl or ether end;

vinyl, allyl or methallyl esters obtained from linear or branched $C_1$–$C_{10}$ or cyclic $C_1$–$C_6$ aliphatic alcohols and/or from aromatic alcohols, preferably $C_1$–$C_6$ alcohols, such as vinyl acetate, vinyl propionate, vinyl benzoate or vinyl tert-butylbenzoate;

N-vinylpyrrolidone; vinylcaprolactam; vinyl-N-alkylpyrroles having 1 to 6 carbon atoms; vinyloxazoles; vinylthiazoles; vinylpyrimidines; vinylimidazoles; and vinyl ketones;

(meth)acrylamides obtained from linear, branched or cyclic aliphatic amines and/or from aromatic amines, preferably $C_1$–$C_{20}$ amines, such as tert-butylacrylamide; and (meth)acrylamides, such as acrylamide, methacrylamide or di($C_1$–$C_4$)alkyl(meth) acrylamides;

olefins, such as ethylene, propylene, styrene or substituted styrene;

fluorinated or perfluorinated acrylic or vinyl monomers, in particular (meth)acrylic esters with perfluoroalkyl units;

monomers comprising an amine functional group in the free or else partially or completely neutralized or else partially or completely quaternized form, such as dimethylaminoethyl (meth)acrylate, dimethylaminoethylmethacrylamide, vinylamine, vinylpyridine or diallyldimethylammonium chloride;

carboxybetaines or sulphobetaines obtained by partial or complete quaternization of monomers comprising ethylenic unsaturation comprising an amine functional group by sodium salts of carboxylic acids comprising a mobile halide (sodium chloroacetate, for example) or by cyclic sulphones (propane sulphone);

silicone-comprising (meth)acrylates or (meth)acrylamides, in particular (meth)acrylic esters comprising siloxane units;

their mixtures.

The particularly preferred monomers are chosen from:

(meth)acrylic esters obtained from linear or branched aliphatic alcohols, preferably $C_1$–$C_{20}$ alcohols;

$C_1$–$C_{20}$ (meth)acrylic esters comprising perfuoroalkyl units;

$C_1$–$C_{20}$ (meth)acrylic esters comprising siloxane units;

(meth)acrylamides obtained from linear, branched or cyclic aliphatic amines and/or from aromatic amines, preferably $C_1$–$C_{20}$ amines, such as tert-butylacrylamide; or (meth)acrylamides, such as acrylamide, methacrylamide or di($C_1$–$C_4$)alkyl(meth) acrylamides;

vinyl, allyl or methallyl esters obtained from linear or branched $C_1$–$C_{10}$ or cyclic $C_1$–$C_6$ aliphatic alcohols;

vinylcaprolactam;

optionally substituted styrene;

their mixtures.

In the context of the present invention, the initiator can be any compound, in particular a molecular or polymeric compound, having at least two atoms and/or groups which are radically transferable by polymerization.

The initiator can in particular be an oligomer or a polymer capable of being obtained by radical polymerization, by polycondensation, by anionic or cationic polymerization or by ring opening.

The transferable atoms and/or groups can be situated at the ends of the polymer chain or along the backbone.

Mention may in particular be made of the compounds corresponding to one of the following formulae:

—$R^{11}$CO—X $R^{11}_xR^{12}_yR^{13}_zC$—$(RX)_t$, in which x, y and z represent an integer ranging from 0 to 4, t an integer ranging from 1 to 4, and x+y+z=4–t;

$R^{13}_xC_6$—$(RX)_y$ (saturated ring with 6 carbons), in which x represents an integer ranging from 7 to 11, y represents an integer ranging from 1 to 5, and x+y=12;

$R^{13}_xC_6$—$(RX)_y$ (unsaturated ring with 6 carbons), in which x represents an integer ranging from 0 to 5, y represents an integer ranging from 1 to 6, and x+y=6;

—[—$(R^{11})(R^{12})(R^{13})C$—(RX)—]$_n$, in which n is greater than or equal to 1; cyclic or linear;

—[—$(R^{12})_xC_6(RX)_y$—$R^{11}$—]$_n$, in which x represents an integer ranging from 0 to 6, y represents an integer ranging from 1 to 6 and n is greater than or equal to 1, with x+y=4 or 6; cyclic or linear;

—[—$(R^{12})_xC_6(RX)_y$—$R^{11}$—]$_n$, in which x represents an integer ranging from 0 to 12, y represents an integer ranging from 1 to 12 and n is greater than or equal to 1, with x+y=10 or 12; cyclic or linear;

—$R^{11}R^{12}R^{13}$Si—X

—[OSi$(R^{11})_x(RX)_y$]$_n$, cyclic or linear, in which x and y represent an integer ranging from 0 to 2 and n is greater than or equal to 1, with x+y=2;

—$R^{11}R^{12}$N—X

—$R^{11}$N—$X_2$ $(R^{11})_xP(O)_y$—$X_{3-x}$, in which x and y represent integers ranging from 0 to 2 and x+y=5;

$(R^{11}O)_xP(O)_y$—$X_{3-x}$, in which x and y represent integers ranging from 0 to 2 and x+y=5;

—[$(R^{11})_tN_zP(O)_x(O$—$RX)_y$—]$_n$, cyclic or linear, in which x represents an integer ranging from 0 to 4, y represents an integer ranging from 1 to 5, z represents an integer ranging from 0 to 2, t represents an integer ranging from 0 to 3 and n is greater than or equal to 1;

in which:

R, $R^{11}$, $R^{12}$ and $R^{13}$ represent, independently of one another, a hydrogen or halogen atom; a linear or branched alkyl radical having 1–20, preferably 1–10 and more preferably 1–6 carbon atoms; a cycloalkyl radical having 3–8 carbon atoms; a —C(=Y)$R^5$, —C(=Y)N$R^6R^7$ or —$R^8_3$Si radical (see the definitions of $R^5$ to $R^8$ above);

COCl; —OH; —CN; an alkenyl or alkynyl radical having 2–20, preferably 2–6, carbon atoms; an oxiranyl or glycidyl radical or an alkylene or alkenylene radical substituted with an oxiranyl or a glycidyl; an aryl, heterocyclyl, aralkyl or aralkenyl radical; or an alkyl radical having 1–6 carbon atoms in which all or part of the hydrogen atoms are substituted either by halogen atoms, such as fluorine, chlorine or bromine, or by an alkoxy group having 1–4 carbon atoms or by an aryl, heterocyclyl, —C(=Y)$R^5$, —C(=Y)N$R^6R^7$, oxiranyl or glycidyl radical;

—X represents a halogen atom, such as Cl, Br or I, or an —OR', —SR, —SeR, —OC(=O)R', —OP(=O)R', —OP(=O)(OR')$_2$, —OP(=O)OR', —O—NR'$_2$, —S—C(=S)NR'$_2$, —CN, —NC, —SCN, —CNS, —OCN, —CNO and —$N_3$ radical, in which R' represents an alkyl radical having 1–20 carbon atoms which is optionally substituted by one or more halogen atoms, in particular fluorine and/or chlorine atoms, and R represents a linear or branched alkyl or aryl radical having 1–20, preferably 1–10, carbon atones, it additionally being possible for the —NR'$_2$ group to represent a cyclic group, the two R' groups being joined so as to form a 5-, 6- or 7-membered heterocycle.

Preferably, X represents a halogen atom and in particular a chlorine or bromine atom.

The initiator is preferably chosen from the compounds of formula $R^{13}_xC_6$—$(RX)_y$ (saturated ring with 6 carbons) in which x represents an integer ranging from 7 to 11, y represents an integer ranging from 1 to 5 and x+y=12;

—[—$(R^{12})_xC_6(RX)_yR^{11}$—]$_n$, in which x represent an integer ranging from 0 to 6, y represents an integer ranging from 1 to 6 and n is greater than or equal to 1, with x+y=4 or 6; cyclic or linear; and —[OSi$(R^{11})_x(RX)_y$]$_n$, cyclic or linear, in which x and y represent an integer ranging from 0 to 2 and n is greater than or equal to 1, with x+y=2.

Mention may in particular be made, as initiator, of the following compounds:

octa(2-isobutyrylbromide)octa(tert-butyl)calix(8)arene, octa(2-propionylbromide)octa(tert-butyl)calix(8)arene, and hexakis(α-bromomethyl)benzene.

The compound comprising a transition metal which is capable of participating in a reduction stage with the initiator and a "dormant" polymer chain can be chosen from those which correspond to the formula $M^{n+}X'_n$, in which formula:

M can be chosen from Cu, Au, Ag, Hg, Ni, Pd, Pt, Rh, Co, Ir, Fe, Ru, Os, Re, Mn, Cr, Mo, W, V, Nb, Ta and Zn, X' can represent a halogen (in particular bromine or chlorine), OH, (O)$_{1/2}$, an alkoxy radical having 1–6 carbon atoms, $(SO_4)_{1/2}$, $(PO_4)_{1/3}$, $(HPO_4)_{1/2}$, $(H_2PO_4)$, a triflate, hexafluorophosphate, methanesulphonate, arylsulphonate, SeR, CN, NC, SCN, CNS, OCN, CNO, $N_3$ and $R'CO_2$ radical, in which R represents a linear or branched alkyl or aryl radical having 1–20, preferably 1–10, carbon atoms and R' represents H or a linear or branched alkyl radical having 1–6 carbon atoms or an aryl radical which is optionally substituted by one or more halogen atoms, in particular fluorine and/or chlorine atoms;

n is the charge on the metal.

The choice is preferably made of M representing copper or ruthenium and X' representing bromine or chlorine.

Mention may in particular be made of copper bromide.

Mention may be made, among the ligands capable of being used in the context of the present invention, of compounds comprising at least one nitrogen, oxygen, phosphorus and/or sulphur atom which are capable of coordinating via a a bond to the compound comprising a transition metal.

Mention may also be made of compounds comprising at least two carbon atoms which are capable of coordinating via a π bond to the compound comprising a transition metal.

Mention may further be made of compounds comprising at least one carbon atom which are capable of coordinating via a σ bond to the compound comprising a transition metal but which do not form a carbon-carbon bond with the monomer during the polymerization, that is to say which do not participate in β-addition reactions with the monomers.

Mention may further be made of compounds capable of coordinating via μ or η bond to the compound comprising a transition metal.

Mention may in particular be made of the compounds of formula:

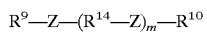

$$R^9-Z-(R^{14}-Z)_m-R^{10}$$

in which:
R$^9$ and R$^{10}$ are, independently of one another, a hydrogen atom; a linear or branched alkyl radical having 1–20, preferably 1–10, carbon atoms; an aryl radical; a heterocyclyl radical; or an alkyl radical having 1–6 carbon atoms which is substituted with an alkoxy radical having 1–6 carbon atoms or a dialkylamino radical having 1–4 carbon atoms or a —C(=Y)R$^5$ or —C(=Y)NR$^6$R$^7$ and/or YC(=Y)R$^8$ radical (see the definitions R$^5$ to R$^8$ and Y above); it being given that R$^9$ and R$^{10}$ can be joined so as to form a saturated or unsaturated ring;

R$^{14}$ represents, independently of one another, a divalent group chosen from alkanediyls having 2–4 carbon atoms; alkenylenes having 2–4 carbon atoms; cycloalkanediyls having 3–8 carbon atoms; cycloalkenediyls having 3–8 carbon atoms; arenediyls and heterocyclylenes;

Z represents O, S, NR$^{15}$ or PR$^{15}$, with R$^{15}$ representing H; a linear or branched alkyl radical having 1–20 carbon atoms; an aryl radical; a heterocyclyl radical; or an alkyl radical having 1–6 carbon atoms which is substituted with an alkoxy radical having 1–6 carbon atoms or a dialkylamino radical having 1–4 carbon atoms or a —C(=Y)R$^5$ or —C(=Y)NR$^6$R$^7$ and/or YC(=Y)R$^8$ radical (see the definitions of R$^5$ to R$^8$ and Y above);

m is between 0 and 6.

Mention may also be made of the compounds of formula:

$$R^{20}R^{21}C[C(=Y)R^5]$$

in which:
R$^{20}$ and R$^{21}$ are, independently of one another, a hydrogen atom; a halogen atom; a linear or branched alkyl radical having 1–20, preferably 1–10, carbon atoms; an aryl radical; or a heterocyclyl radical; it being given that R$^{20}$ and R$^{21}$ can be joined so as to form a saturated or unsaturated ring; it being given that, in addition, each radical can be substituted with an alkyl radical having 1–6 carbon atoms, an alkoxy radical having 1–6 carbon atoms or an aryl radical;

R$^5$ and Y being defined above.

Mention may further be made, as ligands, of carbon monoxide; optionally substituted porphyrins and porphycenes; optionally substituted ethylenediamine and propylenediamine; polyamines with tertiary amines, such as pentamethyidiethylenetriamine; aminoalcohols, such as aminoethanol and aminopropanol, which are optionally substituted; glycols, such as ethylene glycol or propylene glycol, which are optionally substituted; arenes, such as benzene, which are optionally substituted; optionally substituted cyclopentadiene; optionally substituted pyridines and bipyridines; acetonitrle; 1,10-phenanthroline; cryptands and crown ethers; or sparteine.

The preferred ligands are chosen in particular from pyridines and bipyridines which are optionally substituted by $C_2$–$C_{15}$ alkyl radicals, in particular $C_6$–$C_{12}$ radicals and especially the nonyl radical; or polyamines with tertiary amines, such as pentamethyidiethylenetriamine.

The polymerization of the monomers, in the presence of the initiator, of the compound comprising a transition metal and of the ligand which acts as activator, results in the production of a polymer having a star structure, which can be represented by the formula (I) given above, in which the monomers have polymerized to give "n" alike or different polymer chains all connected to a polyfunctional centre A which derives from the initiator.

It has been found that, in order to achieve the goal pursued by the present invention, that is to say to obtain a composition which does not exhibit the disadvantages of the prior art and which is in particular comfortable to apply and to wear while not being sticky to the touch (absence of tack), it is preferable to choose a polymer corresponding to the following criteria:

it preferably comprises one or more monomers Mk the corresponding homopolymer of which exhibits a Tg of greater than or equal to approximately 0° C., preferably of greater than or equal to 5° C. and even better still of greater than or equal to 10° C.;

this or these monomers Mk being present in the final polymer in a minimum amount of approximately 40% by weight, preferably in an amount of between 50 and 99% by weight and even better still in an amount of 60–90% by weight with respect to the total weight of monomers; and the polymer preferably furthermore comprises one or more monomers Mj, the corresponding homopolymer of which exhibits a Tg of less than or equal to approximately 0° C., preferably of less than or equal to –10° C. and even better still of less than or equal to –15° C., this or these monomers Mj being present in the final polymer in a maximum amount of approximately 60% by weight, preferably in an amount of between 1 and 50% by weight and even better still in an amount of 10–40% by weight with respect to the total weight of monomers.

The Tg (glass transition temperature) is measured by DSC (Differential Scanning Calorimetry) according to ASTM Standard D3418-97.

The polymers as defined in the present invention preferably is film-forming or can be rendered film-forming by addition of an additional agent which is able to form a film. The term "film-forming" is understood to mean that the polymer, after application to a substrate and evaporation of the solvent (aqueous or organic), results in a transparent and uncracked film.

Such an additional agent which is able to form a film can be chosen from any compound known to a person skilled in the art as being capable of fulfilling the desired role and can be chosen in particular from plasticizing agents and/or from coalescence agents. Mention may in particular be made, alone or as a mixture, of:

glycols and their derivatives, such as diethylene glycol ethyl ether, diethylene glycol methyl ether, diethylene glycol butyl ether, diethylene glycol hexyl ether, ethylene glycol ethyl ether, ethylene glycol butyl ether or ethylene glycol hexyl ether;

glycerol esters, such as glycerol diacetate (diacetin) and glycerol triacetate (triacetin);

propylene glycol derivatives, in particular propylene glycol phenyl ether, propylene glycol diacetate, propylene glycol methyl ether, propylene glycol ethyl ether, propylene glycol butyl ether, dipropylene glycol methyl ether, dipropylene glycol butyl ether, dipropylene glycol ethyl ether, tripropylene glycol butyl ether or tripropylene glycol methyl ether;

acid esters, in particular carboxylic acid esters, such as citrates, phthalates, adipates, carbonates, tartrates, phosphates or sebacates, oxyethylenated derivatives, such as oxyethylenated oils, in particular vegetable oils, such as castor oil; or oxyethylenated silicone oils.

The amount of additional agent which is able to form a film can be chosen by a person skilled in the art on the basis of his overall knowledge so as to form a film having the desired mechanical properties while retaining, in the composition, cosmetically acceptable properties.

In a preferred embodiment of the invention, a polymer, optionally in combination with additional agents which are able to form a film, is chosen which makes it possible to obtain a film having at least one of the following physico-chemical characteristics:

a modulus of elasticity (Young's modulus) of less than approximately 200 MPa, preferably of between 2 and 100 MPa, preferably of between 5 and 80 MPa;

a hardness of less than 110, preferably of between 1 and 70 and even better still of between 5 and 55. The measurement methods are described before the examples.

The polymers as defined above can be present in the medium in a form dissolved or dispersed in an aqueous, organic or aqueous/organic phase, in particular an alcoholic or aqueous/alcoholic phase, and/or a fatty phase, according to the application envisaged.

The polymers can be present in the composition according to the invention in an amount which can be easily determined by a person skilled in the art according to the application envisaged and which can be between 1 and 50% by weight, on a dry basis, with respect to the total weight of the composition, preferably between 1 and 40% by weight and preferably between 5 and 35% by weight.

The cosmetic or pharmaceutical compositions according to the invention therefore additionally comprise a cosmetically or pharmaceutically acceptable medium which can be chosen by a person skilled in the art according to the application envisaged.

This medium can comprise an aqueous phase and/or a fatty phase. It can also be anhydrous.

The aqueous phase can comprise water and/or a thermal water and/or a spring water and/or a mineral water and/or a floral water.

It can also comprise one or more cosmetically acceptable organic solvents or else a mixture of water and of one or more cosmetically acceptable organic solvents. Mention may be made, among these organic solvents, of:

$C_1$–$C_4$ alcohols, such as ethanol, ispropanol or n-propanol;

ethers, such as dimethoxyethane;

ketones, such as acetone or methyl ethyl ketone;

lower $C_1$–$C_3$ carboxylic acid esters, such as methyl acetate or ethyl acetate.

The fatty phase can comprise conventional volatile or non-volatile oils, gums and/or waxes of animal, vegetable, mineral or synthetic origin, alone or as mixtures, in particular:

linear, branched or cyclic, volatile or non-volatile, silicone oils which are optionally organomodified; phenylated silicones; or silicone resins and gums which are liquid at room temperature;

mineral oils, such as liquid paraffin and liquid petrolatum;

oils of animal origin, such as perhydrosqualene or lanolin;

oils of vegetable origin, such as liquid triglycerides, for example sunflower, maize, soybean, jojoba, gourd, grape seed, sesame, hazlenut, apricot, macadamia, avocado, sweet almond or castor oils, triglycerides of caprylic/capric acids, olive oil, groundnut oil, rapeseed oil or coconut oil;

synthetic oils, such as purcellin oil, isoparaffins, fatty alcohols or esters of fatty acids;

fluorinated and perfluorinated oils or fluorinated silicone oils;

waxes chosen from known animal, fossil, vegetable, mineral or synthetic waxes, such as paraffin waxes, polyethylene waxes, carnauba or candelilla waxes, beeswaxes, lanolin wax, chinese insect waxes, rice wax, ouricury wax, esparto wax, cork fibre wax, sugarcane wax, japan wax, sumach wax, montan wax, microcrystalline waxes, ozokerite, the waxes obtained by the Fischer-Tropsch synthesis, silicone waxes or their mixtures.

The composition can additionally comprise at least one water-soluble dye and/or at least one pigment which are used conventionally in the field of cosmetics and make-up. The term "pigments" should be understood as meaning white or coloured and inorganic or organic particles which are insoluble in the medium and which are intended to colour and/or opacify the composition. The pigments can be present in the composition in a proportion of 0–20% by weight of the final composition and preferably in a proportion of 1–5%. They can be white or coloured, inorganic and/or organic and conventional or nanometric in size. Mention may be made, among inorganic pigments and nanopigments, of titanium, zirconium or cerium oxides, as well as zinc, iron or chromium oxides or ferric blue. Mention may be made, among organic pigments, of carbon black and barium, strontium, calcium or aluminium lakes. Mention may be made, among water-soluble dyes, of the dyes which are standard in the field under consideration, such as the disodium salt of ponceau, the disodium salt of alizarine, quinoline yellow, the trisodium salt of amaranth, the disodium salt of tartrazine, the monosodium salt of rhodamine, the disodium salt of fuchsine or xanthophyll.

Furthermore, the composition according to the invention can comprise adjuvants commonly used in cosmetic or pharmaceutical compositions intended in particular for a topical application. In particular, these compositions can comprise:

- cosmetic and/or pharmaceutical active principles, such as softeners, antioxidants, opacifiers, emollients, hydroxy acids, antifoaming agents, moisturizers, vitamins. fragrances, preservatives, sequestering agents, UV screening agents, ceramides, agents for combating free radicals, slimming agents, bactericides, antidandruff agents, complexing agents, odour absorbers; care active principles, such as agents for combating acne; agents for combating hair loss, antifungal or antiseptic agents, antiperspirants or antibacterials;
- fillers, pearlescent agents, lakes, thickeners, gelling agents, polymers, in particular fixing or conditioning polymers, propellants, basifying or acidifying agents, plasticizers or surfactants;
- additional hydrophilic polymers, such as poly(vinyl alcohol)s and their copolymers, polysaccharides or cellulose polymers, or natural proteins or synthetic polypeptides;
- water-soluble polymers.

Of course, a person skilled in the art will take care to choose this or these optional adjuvants and/or their amounts so that the advantageous properties of the composition according to the invention are not, or not substantially, detrimentally affected by the envisaged addition.

The compositions according to the invention can be provided in various forms and in particular in the form of oil-in-water or water-in-oil emulsions; of aqueous or oily dispersions or of dispersions in a solvent medium; of aqueous or oily solutions or of solutions in a solvent medium; in thickened or gelled fluid form, semi-solid form or soft paste form; or in solid form, such as a stick or tube.

They are preferably provided in the semi-solid, pasty or solid form.

The compositions according to the invention find an application in a large number of cosmetic or pharmaceutical treatments of the skin, hair, eyelashes, eyebrows, nails, mucous membranes or scalp.

They find a very specific application as make-up product for the face or body, in particular as lipstick, foundation, face powder, eyeshadow or alternatively eyeliner and mascara.

An application can also be envisaged in the field of compositions for caring for the skin of the face or body or for the hair, scalp, mucous membranes or semi-mucous membranes; of antisun or self-tanning compositions; of dermatological compositions or of pharmaceutical compositions to be applied to the skin, semi-mucous membranes and/or mucous membranes.

An application can also be envisaged as body hygiene composition, for example in the form of a deodorant stick, or as hair composition, for example as a styling stick.

They are more preferably employed as transfer-free make-up compositions, in particular as a transfer-free lipstick composition, preferably in the solid form, such as a stick, or in the thickened or gelled form, and/or as a transfer-free foundation composition in the solid or semi-solid form, in particular in the compact form, or in the form of an optionally thickened fluid.

The invention is illustrated in more detail in the following examples.

A) Measurement of the Hardness

The hardness of the film is measured according to ASTM Standard D43-66 or NF-T Standard 30-016 (October 1981) using a Persoz pendulum.

The film deposited on the substrate must have a thickness of approximately 300 microns before drying. After drying for 24 hours at 30° C. and under a relative humidity of 50%, a film is obtained which has a thickness of approximately 100 microns; its hardness is then measured at 30° C. and 50% relative humidity.

B) Measurement of the Young's Modulus (or Modulus of Elasticity)

The Young's modulus (modulus of elasticity) is measured according to the standard ASTM Standards, Volume 06.01 D 2370–92, "Standard Test Method for Tensile Properties of Organic Coatings".

The film deposited on the substrate must have a thickness of approximately 300 microns before drying. After drying for 7 days at 21° C. and under a relative humidity of 50%, a film is obtained which has a thickness of approximately 100 microns.

The samples measured have a width of 5 mm and a thickness of 100 microns. The distance between the clamping jaws is 25 mm. The tensioning rate is 1000 mm per minute.

EXAMPLE 1

Preparation of the Initiator

The initiator prepared was 5,11,17,23,29,35,41,47-octa(2-propionylbromide)-49,50,51,52,53,54,55,56-octa(tert-butyl)calix(8)arene (M=2378 g).

The reactants used were as follows:

| | |
|---|---|
| 4-(tert-butyl)calix(8)arene (M = 1298 g), comprising 8 phenol units (Aldrich) | 15 g |
| 2-bromopropionyl bromide of formula $CH_3$—CHBr—COBr | 59.9 g |
| triethylamine | 28 g |
| tetrahydrofuran (THF) | 120 g |

The 4-(t-butyl)calix(8)arene and the solvent THF were added to a round-bottomed flask equipped with a stirrer and a thermometer; the mixture was left stirring for 10 minutes at room temperature.

The triethylamine was subsequently added, which took approximately 15 minutes.

The 2-bromopropionyl bromide, dissolved beforehand in THF, was then added at a temperature of approximately 5° C., which took approximately 1 h 30.

The mixture was left stirring for at least 12 hours at 5° C. and then the temperature was allowed to gradually rise to room temperature.

The solution obtained was concentrated by evaporating the THF. A product was precipitated from a water/ice mixture, extraction was then carried out with ethyl ether and the extract was dried over magnesium sulphate.

The solution obtained was concentrated and a compound was precipitated from a methanol/ice (90/10) mixture in a compound/precipitant ratio of ⅕.

23 g of compound were obtained, i.e. a yield of 85%, which compound existed in the form of a powder.

Characterization was carried out by NMR/GC or HPLC. The compound obtained exhibited values in accordance with those expected.

EXAMPLE 2

Preparation of an 8-Branched Star Polymer, each Branch of which was a Block Copolymer 1) First Stage: Preparation of a Star Polymer with 8 Poly (Tert-butyl Acrylate) Branches The reactants used were as follows:

| | |
|---|---|
| monomer 1: tert-butyl acrylate (Tg = 50° C.) | 100 g |
| monomer 2: lauryl methacrylate (Tg = −20° C.) | 80 g |

| | |
|---|---|
| initiator (prepared according to Example 1) (corresponding to 4 × 10⁻³ mol of RBr) | 1.19 g |
| CuBr (corresponding to 4 × 10⁻³ mol) | 0.57 g |
| Bipyridine (corresponding to 8 × 10⁻³ mol) | 1.25 g |

The monomers were distilled beforehand.

The reactants, except the monomers, were mixed in a sealed and flame-treated reactor comprising a nitrogen inlet and then the monomer 1 was added.

The reactor was heated under nitrogen to approximately 120° C. and reaction was then allowed to take place at 120° C. for 4 hours, the nitrogen inlet being disconnected.

2) Second Stage: Formation of the Second Block at the End of each Branch

The monomer 2 was then added, namely 80 g of lauryl methacrylate. Reaction was again allowed to take place at 120° C. for 4 hours.

After reaction, the reaction mixture was allowed to cool; a viscous green solution was obtained, which solution was dissolved in dichloromethane. The polymer solution was passed through neutral alumina and the clear solution obtained was precipitated from a methanol/water (80/20) mixture in a polymer/precipitant ratio of ⅕.

165 g of polymer were obtained, i.e. a yield of 90%, which polymer existed in the form of a viscous product.

This polymer was a calix(poly(tert-butyl acrylate)-block-poly(lauryl methacrylate))8 block copolymer.

Characterization was carried out by GC:THF linear polystyrene equivalent, light scattering detection: 329,800 g/mol (theoretical mass: approximately 346,400); polydispersity index: 2.

The polymer obtained exhibited values in accordance with those expected.

Young's modulus: 6 MPa
Hardness: 15 s

EXAMPLE 3

Lipstick

A 25% solution in isododecane of the polymer prepared according to Example 2 was prepared.

A lipstick composition was subsequently prepared comprising:

| | |
|---|---|
| 25% solution of the polymer in isododecane | 5 g |
| waxes (carnauba, polyethylene) | 20 g |
| oils (hydrogenated coconut, jojoba, castor) | 35 g |
| isopropyl lanolate | 25 g |
| fillers/pigments | 15 g |

A cosmetically satisfactory composition was obtained which was applied to the lips and which gave a tack-free film.

EXAMPLE 4

Foundation

A 25% solution in isododecane of the polymer prepared according to Example 2 was prepared.

A foundation composition was subsequently prepared comprising:

| | |
|---|---|
| 25% solution of the polymer in isododecane | 82 g |
| Nylon powder | 8 g |
| titanium oxide | 8 g |
| iron oxide | 2 g |

A foundation was obtained which was applied to the neck and face. The make-up was natural and was not uncomfortable. It did not transfer and was resistant to water.

A cosmetically satisfactory composition was obtained which was applied to the lips and which gave a tack-free film.

EXAMPLE 4

Foundation

A 25% solution in isododecane of the polymer prepared according to Example 2 was prepared.

A foundation composition was subsequently prepared comprising:

| | |
|---|---|
| 25% solution of the polymer in isododecane | 82 g |
| Nylon powder | 8 g |
| titanium oxide | 8 g |
| iron oxide | 2 g |

A foundation was obtained which was applied to the neck and face. The make-up was natural and was not uncomfortable. It did not transfer and was resistant to water.

What is claimed is:

1. A composition, comprising, in a physiologically acceptable medium, at least one polymer having a star structure chosen from structures of formula (I):

A-[(M1)$_{p1}$-(M2)$_{p2}$ . . . (Mi)$_{pj}$]$_n$     (I)

in which:

A is chosen from polyfunctional centers having a functionality n; [(M1)$_{p1}$-(M2)$_{p2}$ . . . (Mi)$_{pj}$] represents a branch comprising at least one polymerized monomeric unit Mi having a polymerization index pj;

n is an integer greater than or equal to 2;

pj is greater than or equal to 2;

there are at least two branches which may be identical or different; and said at least two branches are grafted covalently to A;

wherein said at least one polymerized monomeric unit Mi comprised by at least one of said at least two branches is chosen from polymerized monomeric units Mk, which may be identical or different, wherein a homopolymer formed by the corresponding polymerized monomeric units Mk has a Tg of greater than or equal to 0° C.; and wherein said at least one polymerized monomeric unit Mi contained by at least one of said at least two branches is chosen from polymerized monomeric unit Mj, which may be identical or different, wherein a homopolymer formed by the corresponding polymerized monomeric units Mj has a Tg of less than or equal to 0° C.;

wherein said composition is in the form of a make-up product for the face or body chosen from lipsticks, foundations, face powders, eyeshadows, eyeliners, and mascaras.

2. A composition according to claim 1, wherein said at least one polymerized monomeric unit Mi chosen from polymerized monomeric units Mk is present in an amount greater than or equal to 40 percent by weight relative to the total weight of the polymerized monomeric units Mi.

3. A composition according to claim 1, wherein said at least one polymerized monomeric unit Mi chosen from polymerized monomeric units Mj is present in an amount less than or equal to 60 percent by weight relative to the total weight of the polymerized monomeric units Mi.

4. A composition according to claim 1, wherein said physiologically acceptable medium is chosen from pharmaceutically acceptable mediums and cosmetically acceptable mediums and further wherein said composition is chosen from forms of pharmaceutical compositions and cosmetic compositions.

5. A composition according to claim 1, further comprising at least one agent which is able to form a film.

6. A composition according to claim 5, wherein said at least one agent is chosen from plasticizing agents and coalescence agents.

7. A composition according to claim 1, wherein said at least one polymer is present in an amount ranging from 1 to 50 percent by weight, on a dry basis, with respect to the total weight of said composition.

8. A composition according to claim 7, wherein the range is from 1 to 40 percent by weight.

9. A composition according to claim 7, wherein the range is from 5 to 35 percent by weight.

10. A composition according to claim 1, wherein said at least one polymer is present in said physiologically acceptable medium containing at least one phase chosen from aqueous phases, organic phases, aqueous/organic phases, and fatty phases.

11. A composition according to claim 10, wherein said at least one phase is chosen from alcoholic and aqueous/alcoholic phases.

12. A composition according to claim 10, wherein said at least one polymer is dissolved or dispersed in said at least one phase.

13. A composition according to claim 1, wherein said composition has a form chosen from oil-in-water emulsions; water-in-oil emulsions; dispersions in a solvent medium; solutions in a solvent medium; thickened fluids; gelled fluids; semi-solids; paste forms; and solid forms.

14. A composition according to claim 13, wherein said solid forms are chosen from sticks and tubes.

15. A composition according to claim 1, wherein said make-up product is transfer-free.

16. A process for treating a keratinous substance, comprising applying to said keratinous substance a composition, comprising, in a physiologically acceptable medium, at least one polymer having a star structure chosen from structures of formula (I):

A-[(M1)$_{p1}$-(M2)$_{p2}$ ... (Mi)$_{pj}$]$_n$      (I)

in which:

A is chosen from polyfunctional centers having a functionality n; [(M1)$_{p1}$-(M2)$_{p2}$ ... (Mi)$_{pj}$] represents a branch comprising at least one polymerized monomeric unit Mi having a polymerization index pj;

n is an integer greater than or equal to 2;

pj is greater than or equal to 2;

there are at least two branches which may be identical or different; and said at least two branches are grafted covalently to A;

wherein said at least one polymerized monomeric unit Mi comprised by at least one of said at least two branches is chosen from polymerized monomeric units Mk, which may be identical or different, wherein a homopolymer formed by the corresponding polymerized monomeric units Mk has a Tg of greater than or equal to 0° C.; and wherein said at least one polymerized monomeric unit Mi contained by at least one of said at least two branches is chosen from polymerized monomeric unit Mj, which may be identical or different, wherein a homopolymer formed by the corresponding polymerized monomeric units Mj has a Tg of less than or equal to 0° C.

17. A process according to claim 16, wherein said at least one polymerized monomeric unit Mi chosen from polymerized monomeric units Mk is present in an amount greater than or equal to 40 percent by weight relative to the total weight of the polymerized monomeric units Mi.

18. A process according to claim 16, wherein said at least one polymerized monomeric units Mi chosen from polymerized monomeric units Mj is present in an amount less than or equal to 60 percent by weight relative to the total weight of the polymerized monomeric units Mi.

19. A process according to claim 16, wherein said keratinous substance is chosen from skin, hair, scalp, eyelashes, eyebrows, nails, and lips.

20. A process according to claim 19, wherein said keratinous substance is chosen from human keratinous substances.

21. A process for preparing the composition according to claim 1, comprising introducing, in a physiologically acceptable medium, said at least one polymer according to claim 1.

22. A process according to claim 21, wherein said at least one polymerized monomeric unit Mi chosen from polymerized monomeric units Mk is present in an amount greater than or equal to 40 percent by weight relative to the total weight of the polymerized monomeric units Mi.

23. A process according to claim 22, wherein said at least one polymerized monomeric units Mi chosen from polymerized monomeric units Mj is present in an amount less than or equal to 60 percent by weight relative to the total weight of the polymerized monomeric units Mi.

* * * * *